(12) United States Patent
Al Moussalami

(10) Patent No.: US 9,793,100 B2
(45) Date of Patent: Oct. 17, 2017

(54) PORTABLE PLASMA BASED DIAGNOSTIC APPARATUS AND DIAGNOSTIC METHOD

(76) Inventor: Samir Al Moussalami, Montreal (CA)

( * ) Notice: Subject to any disclaimer, the term of this patent is extended or adjusted under 35 U.S.C. 154(b) by 1312 days.

(21) Appl. No.: 13/001,104

(22) PCT Filed: Jul. 23, 2009

(86) PCT No.: PCT/CA2009/001045
§ 371 (c)(1),
(2), (4) Date: Dec. 23, 2010

(87) PCT Pub. No.: WO2010/009555
PCT Pub. Date: Jan. 28, 2010

(65) Prior Publication Data
US 2011/0105339 A1    May 5, 2011

Related U.S. Application Data

(60) Provisional application No. 61/129,844, filed on Jul. 23, 2008.

(51) Int. Cl.
*H01J 49/26* (2006.01)
*H01J 49/00* (2006.01)
*G01N 33/68* (2006.01)

(52) U.S. Cl.
CPC ...... *H01J 49/0022* (2013.01); *G01N 33/6848* (2013.01)

(58) Field of Classification Search
None
See application file for complete search history.

(56) References Cited

U.S. PATENT DOCUMENTS

| 7,069,152 | B2 | 6/2006 | Skilling | |
|---|---|---|---|---|
| 8,546,082 | B2 * | 10/2013 | Hall et al. | 435/6.12 |
| 2003/0028932 | A1 | 2/2003 | Skilling | |
| 2009/0155766 | A1 * | 6/2009 | Goldman | G01N 33/6851 435/4 |

FOREIGN PATENT DOCUMENTS

| CN | 101206204 A | 6/2008 |
|---|---|---|
| KR | 20040032212 A | 4/2004 |
| WO | 03/106997 A1 | 12/2003 |
| WO | 2005/040985 A2 | 5/2005 |

OTHER PUBLICATIONS

Falkner et al (2007 J. Am. Mass Spectrom. 18:850-5).*
Chien et al (1993 Anal Chem 65:1916-24).*
International Search Report: PCT/CA2009/001045.
Canadian Office Action dated Apr. 12, 2013; Appln. No. 2,726,111.

* cited by examiner

*Primary Examiner* — Christopher M Gross
(74) *Attorney, Agent, or Firm* — Praxis

(57) ABSTRACT

A portable plasma based diagnostic apparatus comprising a plasma source for producing energy projectiles at atmospheric pressure, a mass analyzer, a sampling interface for receiving direct sample to be analyzed, the sampling interface being positioned between the plasma source and the mass analyzer, a database containing a library of biomarkers with their associated mass spectra, a processor operatively connected to the plasma source, the mass analyzer and the database. The processor is so configured so as to obtain from the mass analyzer a sample mass spectrum of parent and fragment ions resulting form the collision between the energetic projectiles and the sample, compare the sample mass spectrum with mass spectra in the reference library in order to identify at least one indicator and provide a report based on the at least one identified indicator.

12 Claims, 5 Drawing Sheets

PORTABLE PLASMA BASED DIAGNOSTIC APPARATUS AND DIAGNOSTIC METHOD

CROSS-REFERENCE TO RELATED APPLICATION

This application claims the benefits of U.S. provisional patent applications No. 61/129,844 filed Jul. 23, 2008; which is hereby incorporated by reference.

TECHNICAL FIELD

The present invention relates to a portable plasma based diagnostic apparatus and diagnostic method. The present invention further relates to a portable plasma, atomic, ionic and photonic based diagnostic apparatus and diagnostic method.

BACKGROUND

The quality of health care is founded on complete and accurate information about the patient.

Presently, four main diagnostic modalities are used in hospitals: X-ray, including computed tomography, magnetic resonance imaging, radiopharmaceutical imaging and ultrasound.

Computed tomography (CT) is a medical imaging method employing tomography. Digital geometry processing is used to generate a three-dimensional image of the inside of an object from a large series of two-dimensional X-ray images taken around a single axis of rotation. CT produces a volume of data which can be manipulated, through a process known as windowing, in order to demonstrate various structures based on their ability to block the X-ray beam.

Magnetic resonance imaging (MRI) is a medical imaging technique primarily used in Radiology to visualize the structure and function of the body. It provides detailed images of the body in any plane. MRI provides much greater contrast between the different soft tissues of the body than does computed tomography (CT), making it especially useful in neurological, musculoskeletal, cardiovascular, and oncological imaging. Unlike CT it uses no ionizing radiation, but uses a (powerful) magnetic field to align the nuclear magnetization of (usually) hydrogen atoms in water in the body.

Radiopharmacology is the study and preparation of radiopharmaceuticals, which are radioactive pharmaceuticals. Radiopharmaceuticals are used in the field of nuclear medicine as tracers in the diagnosis and treatment.

Medical sonography (ultrasonography) is an ultrasound-based diagnostic medical imaging technique used to visualize muscles, tendons, and many internal organs, their size, structure and any pathological lesions with real time tomographic images. It is also used to visualize a fetus during routine and emergency prenatal care. Ultrasound is one of the most widely used diagnostic tools in modern medicine.

Increasing demand for medical diagnostics is being driven by the aging population and the rise in prevalence of age-related diseases such as cancer, Alzheimer's disease, stroke, heart failure, etc. These diseases represent the highest cost burden to healthcare systems in industrialized nations, and there is tremendous pressure to develop tests that can assist in earlier diagnosis and aid selection of the most appropriate treatments in order to reduce costs. Hospitals are looking to purchase cost-efficient and more specialized medical equipment that will require fewer medical staff and reduce patients' length of hospital stay.

Despite recent spectacular advances in medicine, mortality rates for the most prevalent cancers have not been significantly reduced. In terms of primary prevention, we do not as yet have at hand robust strategies for these metabolic disorders or diseases.

Thus, there is a need for a simple, portable, noninvasive, rapid, accurate, easy to use, inexpensive and safe diagnostic apparatus to help health care providers to diagnose automatically and in real-time risk or presence of health issues such as, for example, infection, cancer, malignancy diseases or metabolic disorder in order to allow health care providers to take decisions at faster rate and react quickly and appropriately to prognosis or disease risk.

SUMMARY

The present invention relates to a spectrometry plasma, atomic, ionic and photonic-based apparatus that provides in real time and automatically clinicians and healthcare providers with early patient diagnostic of infection, presence of cancer or malignancy diseases by recording the signature of his or her biological tissue (skin), saliva, blood or urine. It enables earlier diagnosis, infection, pre-symptomatic disease detection and disease prevention. It improves operational capabilities for prevention and helps health care providers to take decisions at faster rate and to react quickly and appropriately to symptomatic, pre-symptomatic malignancy diseases, infection or metabolic disorder.

The apparatus is based on a miniaturized atmospheric soft ionization source coupled to miniaturized mass spectrometer. The quantum transfer energy source is coupled to a fast mass spectrometer, for example time of flight, quadrupole or ion-trap, to produce fingerprinting and quantitative measurements of the patient's chemical and biological compounds. The apparatus provides both a quantitative and a qualitative analysis, generating identification of the substances of interest and diagnostic information regarding metabolic disorder, cancer or infectious (malignancy) disease risk possibilities.

The ion source combines selective ionization with selective fragmentation, which provides exceptional detection limits. Increased sensitivity and decreased background allow for low detection limits and false positives diminution. Using different quantum energy beam (plasma, atoms, photons, electrons or ions) as well as direct introduction of divers patient specimens (skin, blood, urine or saliva) strongly enhance structural elucidation, mass spectral chemical and biological information, and specificity. Spectra are highly reproducible and do not require sample pre-treatment, leading to speed of analysis. There is no matrix to complicate matters. Thus eliminating potential losses and excessive handling, which also limits contaminations that can invalidate results. Contaminations are also minimized by direct sample introduction. Eliminating sample preparation gives an added advantage, especially to medical healthcare providers. It also offers for simplicity, along with limited exposure.

An operating process provides secure control of the overall apparatus and simplifies its use by non expert personnel. Reference libraries and automated interpretation of the raw data provide quantification and identification of the chemical and biological compounds as well as diagnostic information regarding malignancy diseases or risk thereof from the patient's sample(s).

More specifically, in accordance with the present invention, there is provided a portable plasma based diagnostic apparatus, comprising:

a miniature atmospheric plasma source for producing energetic projectiles;

a miniature high pressure environment mass analyzer;

an atmospheric direct sample introduction interface for receiving a sample to be analyzed, the atmospheric direct sample introduction interface being positioned between the plasma source and the mass analyzer;

a database containing a reference library of indicators with their associated mass spectra;

a processor operatively connected to the plasma source, the mass analyzer and the database, the processor being so configured so as to:

obtain from the mass analyzer a sample mass spectrum of parent and fragment ions resulting form the collision between the energetic projectiles and the sample;

compare the sample mass spectrum with mass spectra in the reference library in order to identify at least one indicator; and provide a report based on the at least one identified indicator.

In accordance with the present invention, there is also provided a plasma based diagnostic method, comprising:

projecting a beam of energetic projectiles at a sample to be analyzed;

recording a sample mass spectrum of parent and fragment ions resulting form the collision between the energetic projectiles and the sample;

comparing the sample mass spectrum with mass spectra of a reference library in order to identify at least one indicator; and providing a report based on the at least one identified indicator.

BRIEF DESCRIPTION OF THE FIGURES

Embodiments of the invention will be described by way of example only with reference to the accompanying drawings, in which.

DEFINITIONS

The detailed description and figures refer to the following terms which are herein defined:

Analyte: A sample being analyzed, the sample being solid, liquid or gaseous. Examples of analytes include biological tissue (skin), saliva, blood or urine. Other examples may include air or soil samples, etc.

Analyte ion: Ions resulting from the collision between an energetic projectile and an analyte. These ions may be parent ion or various ions resulting from fragmentation.

Analyte profile: The mass spectrum resulting from the collision between an energetic projectile and an analyte.

Sample spectrum: The mass spectrum resulting from the collision between an energetic projectile and an analyte including the background spectrum.

Parent ion pattern: The mass spectrum resulting from the collision between low energy projectiles and an analyte. This spectrum results from the loss of an electron in the analyte molecule.

Fragmentation ion pattern: The mass spectrum resulting from the collision between high energy projectiles and an analyte. This spectrum results from the decomposition of the parent ion or its instability.

Biomarkers: Specific molecules observed in infectious or carcinogenic diseases.

DETAILED DESCRIPTION

Generally stated, the non-limitative illustrative embodiment of the present invention provides a portable plasma, atomic, ionic, electronic and photonic based diagnostic apparatus that provides to clinicians and healthcare providers, in real time and automatically, early patient diagnostic of infection, metabolic disorder, presence of cancer or malignancy diseases by scanning, recording the chemical and/or biological signature(s) of his or her biological tissue (skin), saliva, blood or urine and automatically analyzing obtained spectra for various medical conditions.

Figure 1:
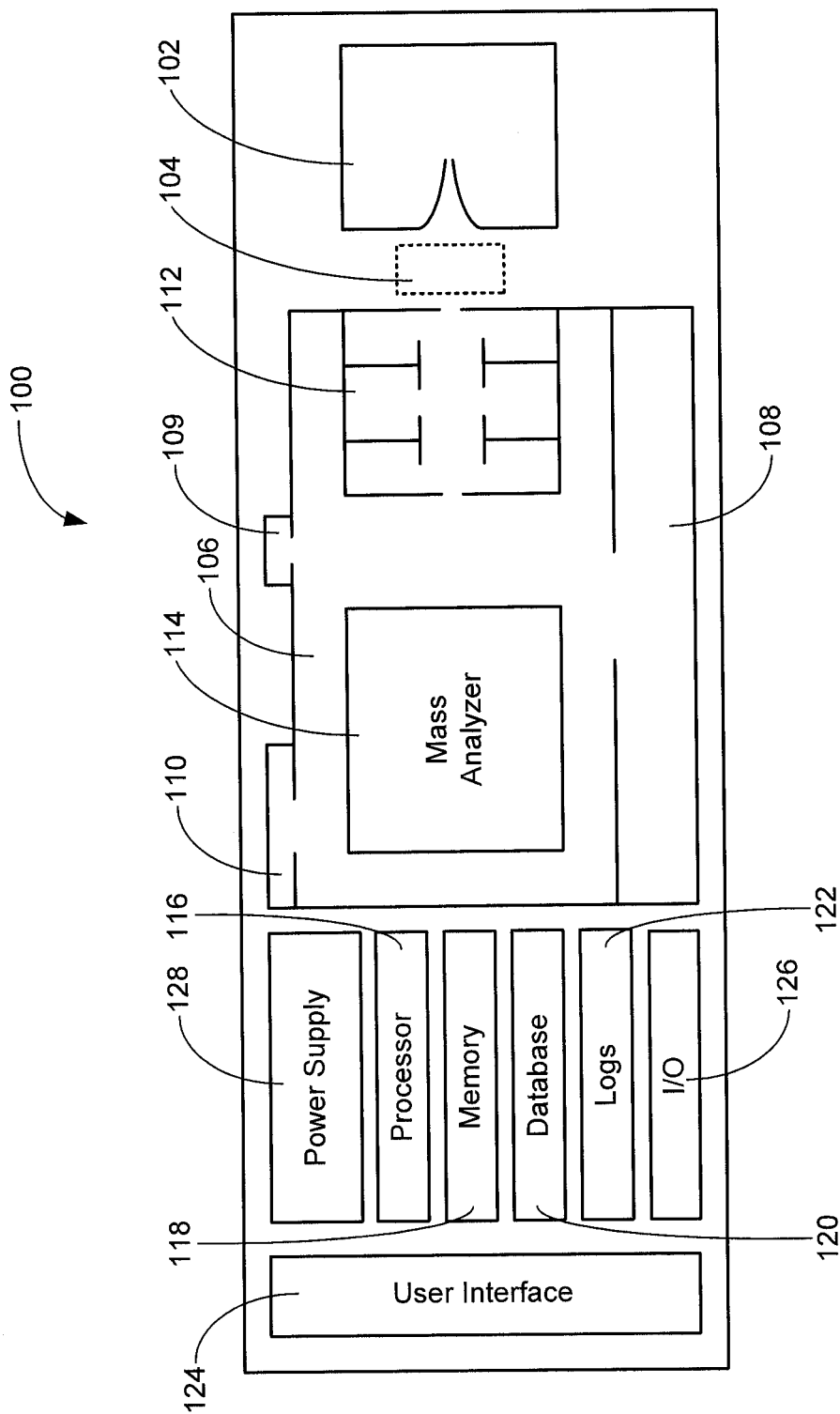
FIG. 1 is a block diagram of a portable ion based diagnostic apparatus according to an illustrative embodiment of the present invention.

Referring to FIG. 1, there is shown a portable plasma, atomic, ionic, electronic and photonic based diagnostic apparatus 100 according to an illustrative example of the present invention. The diagnostic apparatus 100 generally comprises a continued or pulsed miniature atmospheric plasma source 102, a direct sample introduction interface 104, an analyzer chamber 106, a processor 116 with an associated memory 118, a database 120, logs 122, a user interface 124, an input/output interface 126 and a power supply 128. The analyzer chamber 106 includes a miniature vacuum pump 108, a pressure gauge 109, a high pressure ions detector 110, ion extraction and transport lenses 112, and a miniature high pressure environment mass analyzer 114

The plasma source 102 can have, for example, ca. 0.175 $cm^3$ as volume or less, with gas density of ca. $10^{13}$-$10^{15}$ particles/$mm^3$ and a downstream flow of ca. $10^{16}$-$10^{19}$ particles/sec. Depending on the selected application, the processor 116 adjusts the settings of the plasma source 102, which produces the energetic projectile beam that transfers quantum energy to the analyte to form the free (radical) ions. The plasma source 102 may be based on technologies such as, for example, arc-discharge, chemical, Penning or Niers-Bernas ionization processes. As well, fast atom bombardment, lasers and ultraviolet lamps may also be used.

The direct sample introduction interface 104 consists in a free atmospheric interface between the plasma source 102 and the analyzer chamber 106. The patient specimens, i.e. biological tissue (skin), blood drop, saliva or urine (wet cotton), which do not require pre-treatment, are directly introduced into the direct sample introduction interface 104, perpendicularly to the energetic beam emitted by the plasma source 102. The absence of pre-treatment has the benefit of minimizing sample waste and excessive handling, which causes losses. It also limits the risk of contamination that can invalidate results. In an alternative embodiment, the direct sample introduction interface 104 may be provided with a needle mechanism in order to automatically take a blood sample. It may be also provided with water or alcohol beams and a heat interface for contamination cleaning and sterilization.

Ions formed from the collisions of the energetic beam with the analyte directly introduced into the direct sample introduction interface 104 generate fingerprinting of the complex chemical and biological system of the patient, and are extracted and transferred through the ion extraction and transport lenses 112 to the mass analyzer 114 with associated high pressure ions detector 110 using a high differential electric field. The mass analyzer 114, which is located within the analyzer chamber 106, analyzes and records the parent and/or fragmentation ion patterns, which are reproducible for a given energy level and a given sample. The mass analyzer 114 may be based on technologies such as, for example, miniature high performance ion-traps, quadrupoles or time-of-flight (TOF), which may be operated in a high pressure environment, for example $10^{-4}$ to $10^{-1}$ mbar.

During a collision, an electron is ejected into continuum leading to ionization. The ejected electron can take a range of kinetic energies that is defined by the species, i.e. the nature of the analyte and the quantum transfer energy beam involved in the collision. The presence of fragment ions is governed by the excitation energy and the nature of the sample (i.e. analyte or patient specimens). The plasma source 102 allows precise control over fragmentation and yields very reproducible mass spectra. Parent and fragment ions are used for the identification of constituents in complex mixtures.

The analyzer chamber 106 consists in a small differential pumping chamber, for example ca. 1.6 I, which keeps the mass analyzer 114 at pressures of, for example $10^{-4}$ to $10^{-1}$ mbar, using the miniature vacuum pump 108. The analyzer chamber 106 also includes the high pressure ions detector 110 and the ions extraction and transport lenses 112, which are electrostatic lenses. The ion extraction and transport lenses 112 consist in two plate electrodes biased at high differential voltage used downstream of the direct sample introduction interface 104 to extract the analyte ions. Thin coaxial cylinders, on axis, downstream of the extraction electrodes are used to transport and focus the extracted analyte ions at the entrance of the mass analyzer 114 in order to determine the composition of the ion beam.

The peaks in the spectra recorded by the mass analyzer 114 correspond to different mass-dependent velocities (i.e. different mass-to-charge ratios (m/z)) of the ionized sample and are analyzed using a diagnostic process which will be further detailed below. The diagnostic process uses the mass spectrum of the parent and fragment ions, and their relative abundances, provided by the mass analyzer 114 for both the quantization and identification of the analyte composition of the sample in order to establish the patient's analyte profile.

To provide a diagnosis, the established analyte profile of the patient is compared to those of healthy people of the reference library, which is stored in the database 120, in order to identify abnormal peaks. The peaks may be identified by first calculating the mass-to-charge ratios (m/z) and normalizing the spectrum with regard to the total ion currents. The background is then filtered out from the spectrum and peaks detected with an automatic peak detection process. The peak detection process allows for the evaluation of each peak for its contribution into the spectrum, i.e. the relative abundance of each peak in the spectrum. This process may also incorporates a spectral de-convolution sub-process which takes into account discrimination or interference between elements and isotope ratios.

The identified peaks are then used to search the reference library in order to determine a related biomarker. The reference library contains chemical and biological reference materials over a variety of concentrations, well below the limits of detection required. It also contains a chemical and biological database of diseases, along with an ability to create novel chemical and biological sub-libraries. The reference materials may be provided, for example, by federal, provincial and healthcare provider partners.

Optionally, the various test results, error conditions, alarm conditions, etc., may be recorded in logs 122.

The user interface 124 may be used to automatically operate the diagnostic apparatus 100, provide instructions to the user as to how to operate the diagnostic apparatus 100 and display various information such as, for example, user menus, alarms and diagnostic results.

The input/output interface 126 may be used to, for example, update the library, export logs or provide diagnostic results to a further system or storage medium.

The power supply 128 may be, for example, a battery (such as a 9, 12 or 24 Volts battery) to allow the diagnostic apparatus 100 to be portable. The power supply 128 may also be provided with the capability to be directly powered by a 110 or 220 Volts AC power source.

Figure 2A:
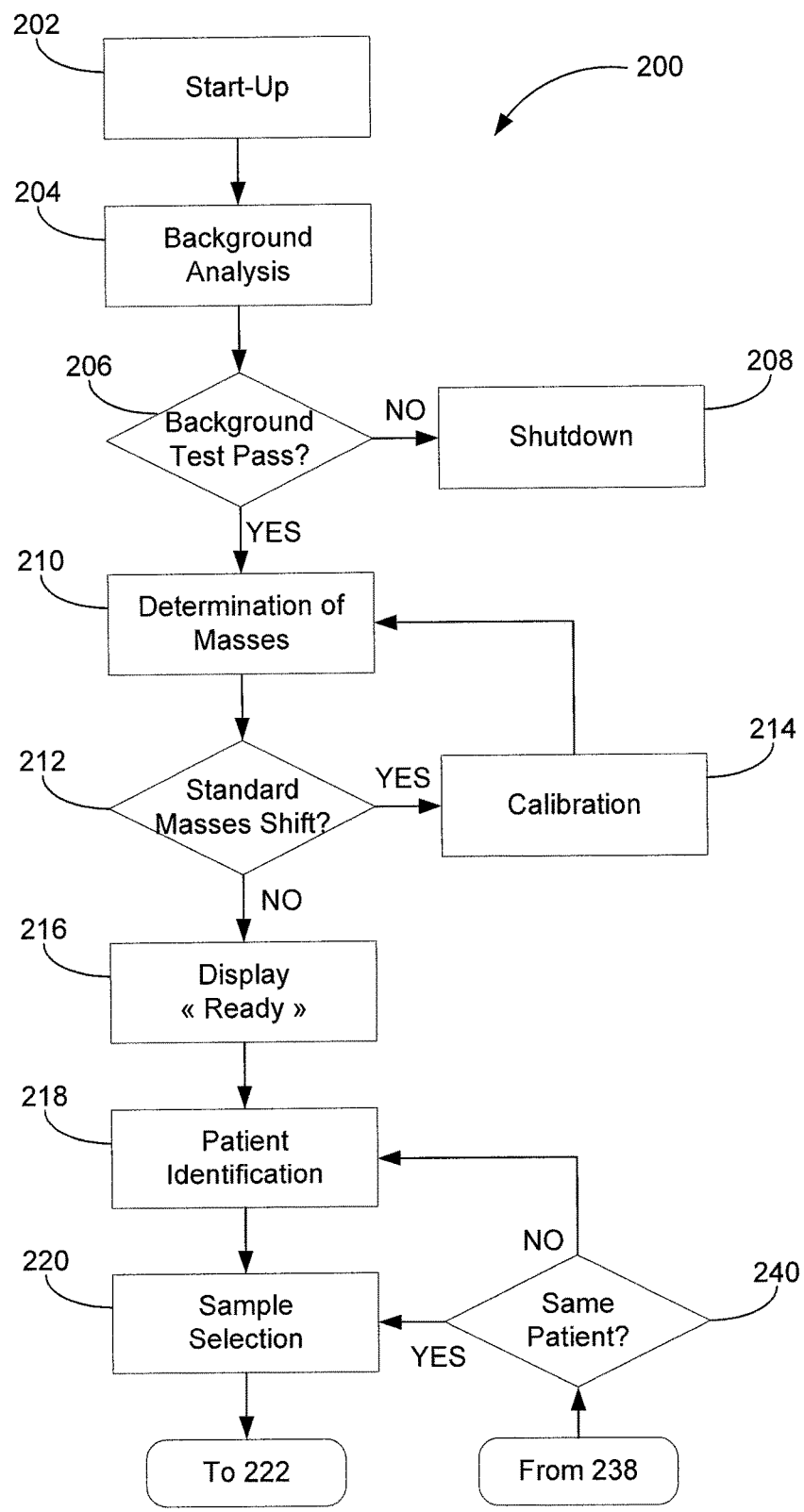
FIGS. 2A and 2B is a flow diagram of an example of an operating process that can be used by the apparatus of FIG. 1.
Figure 2B:
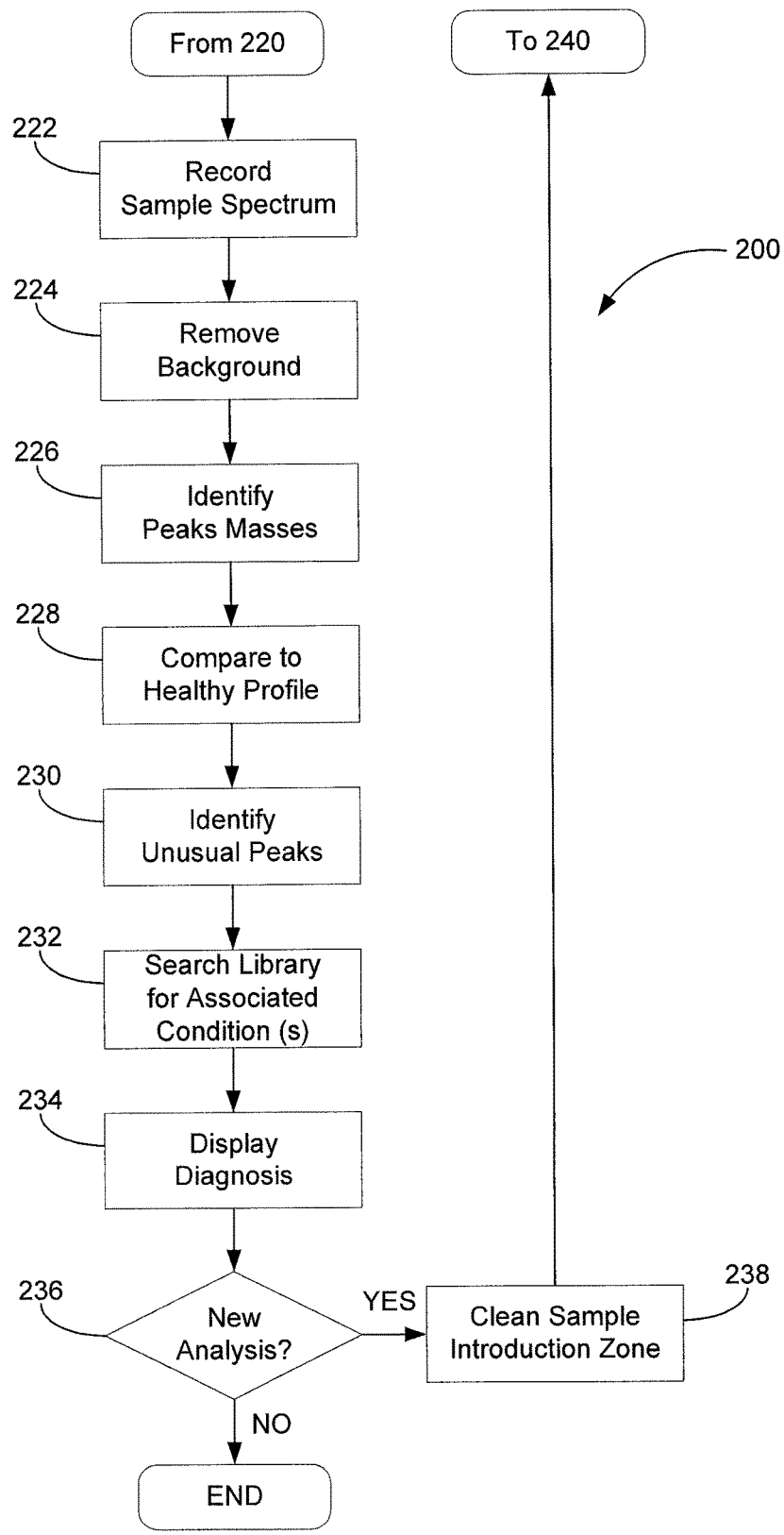

Referring now to FIGS. 2A and 2B, there is shown a flow diagram of an example of an operating process 200 that may be executed by the processor 116 of the diagnostic apparatus 100 of FIG. 1. The steps of the process 200 are indicated by blocks 202 to 240.

The process 200 starts at block 202 where the start-up sequence is initiated, namely the plasma source 102 is powered up and stabilized, the vacuum pump is activated 108 and once the pressure gauge 130 reads a pressure around $10^{-2}$ mbar within the analyzer chamber 106, the ions extraction and transport lenses 112 and mass analyzer 114 are powered up. It is to be understood that complimentary sub-processes may be executed at this point in order to verify the proper functioning of the various components of the diagnostic apparatus 100.

At block 204, the process 200 executes a background (i.e. the environment in which the diagnostic apparatus 100 is used) test in order to determine if there are any contaminants present. This allows the diagnostic apparatus 100 to be also used as an indoor air quality or environment monitor. The background test will be further detailed below.

Then, at block 206, the process 200 verifies if the background test has passed. If it has failed, the diagnostic apparatus 100 analyses and identifies the chemical and biological contaminants of the environment and alerts the end users, then shutdowns at block 208. If it has passed, the process proceeds to block 210.

At block 210, the masses of the various components present in the background are determined and, at block 212, the process verifies if the peaks of the background spectrum are shifted in mass. If so, at block 214, the shifts are computed and the mass analyzer 114 is calibrated, after which the process 200 returns to block 210. If there is no shift in mass of the peaks, the process 200 proceeds to block 216

At block 216, the user interface 124 indicates that the diagnostic apparatus 100 is ready.

Then, at block 218, the process 200 asks for the patient's identification, either by reference to some identification number or by entering the patient's information using the user interface 124. Once the patient has been identified, the process 200 then asks, at block 220, for the type of analysis to be performed, i.e. skin, blood, urine or saliva.

At block 222, the process 200 detects the presence of a sample in the direct sample introduction interface 104 and then starts to record the sample spectrum. Alternatively, the recording may be activated manually. The recorded spectrum may then be stored in the database 120 with the patient's identification and the logs 122 updated.

Then, at block 224, the background spectrum recorded at start-up is subtracted from the recorded sample spectrum. The peaks of the resulting spectrum, the analyte profile, are analyzed and identified at block 226. Following this, at block 228, the identified peaks are compared to those of the analyte profiles of healthy patients stored in the database 120 in order to identify, at block 230, abnormal peaks in the patient's biological and chemical fingerprint (i.e. analyte profile).

At block 232, the process 200 searches through the reference library in order to identify one or more spectra for the given sample type, identified at block 220, having similar peak and mass patterns, each pattern corresponding to a given condition. Each element of the peak and mass pattern, alone or in combination, corresponding to one or more biomarkers, which are associated with a probability of a condition being present.

At block 234, the process 200 establishes a diagnostic using the one or more conditions identified at block 232. This is accomplished taking into consideration each pattern's fit with the identified abnormal peaks as well as probabilities associated with each condition. Furthermore, if multiple types of samples have been analyzed, i.e. skin, blood, urine or saliva, then the results of each analysis can be combined to provide a more accurate diagnosis by enhancing structural elucidation, mass spectral or chemical information and increase sensitivity and specificity, and confirm or complete the pre-diagnosis. The diagnosis can take the form of, for example, a table with the detected masses or molecules, abnormal peaks, their abundance, their identified patterns with corresponding conditions and probabilities. The diagnosis may then be stored in the database 120 along with the patient's information and the logs 122 updated.

Basically, the mass spectrum for parent and fragment ions, and their relative abundance, is used for both the quantization and identification of the chemical and biological composition of a patient's sample. The obtained mass spectrum is first compared to those of healthy profiles in order to isolate abnormalities. The identified abnormalities are then compared to a library of known biomarkers. Each contribution into the spectrum is evaluated taking into account discrimination or interference between elements and isotope ratios. The abundance of resulting biomarkers then allows the generation of an appropriate diagnosis. The biomarkers may also be compared to those present in individuals having a similar profile.

The use of different beams (i.e. plasma, atoms, photons, electrons or ions), with different quantum energies, as well as different patient specimens (i.e. skin, blood, urine or saliva) strongly enhances structural elucidation, mass spectral, chemical or biological information, resulting in highly increased sensitivity, specificity and strongly confirms or completes a pre-diagnosis.

Figure 4:
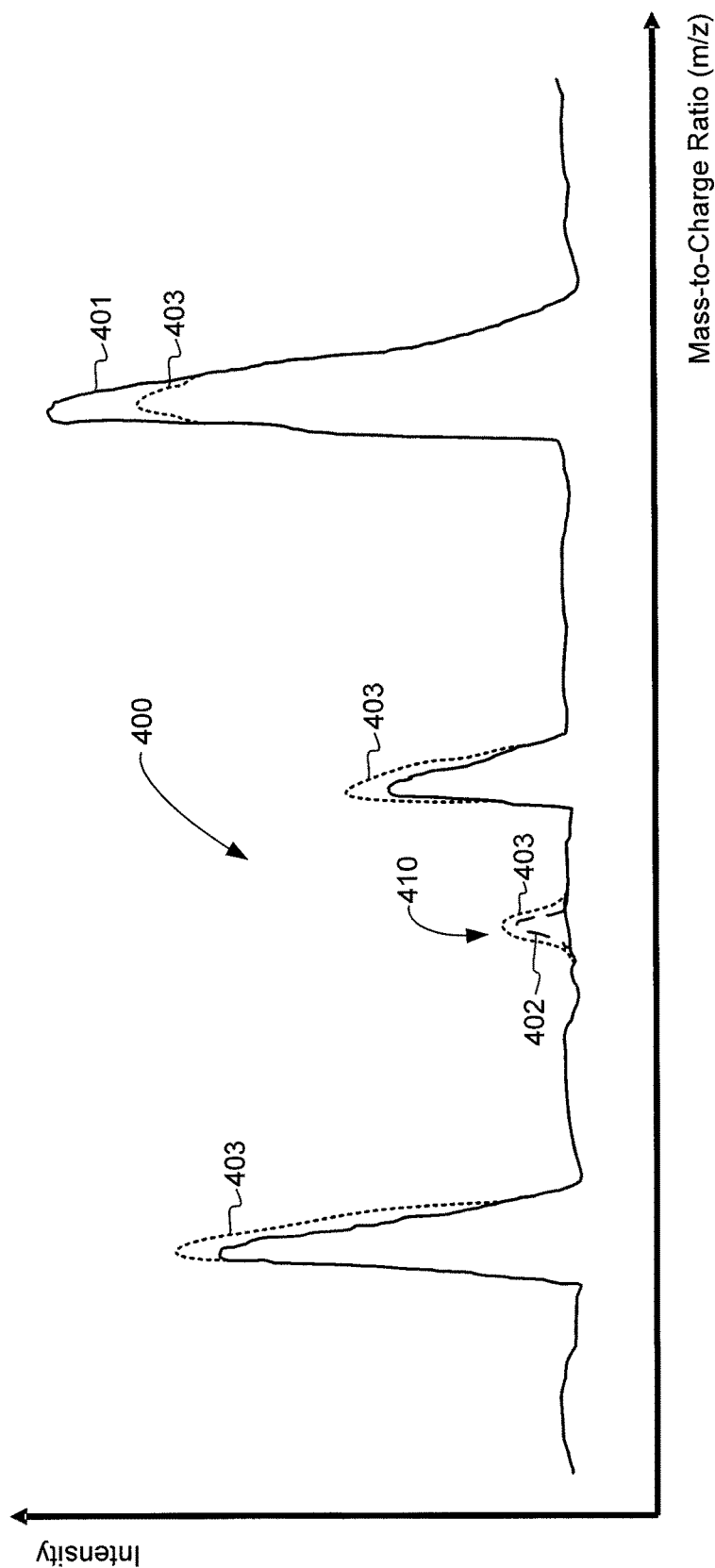
FIG. 4, is a graph of an example of an analyte profile of a patient using high energy projectiles such as energetic helium atoms (~20 eV), the analyte profile of the same patient using low energy projectiles such as energetic nitrogen atoms (~8 eV) and a reference analyte profile of a healthy individual using high energy projectiles such as energetic helium atoms (~20 eV).

Referring to FIG. 4, there is shown an example of a graph 400 of an analyte profile of a patient using high energy projectiles such as energetic helium atoms (~20 eV) 403, the analyte profile of the same patient using low energy projectiles such as energetic nitrogen atoms (~8 eV) 402 and a reference analyte profile of a healthy individual using high energy projectiles such as energetic helium atoms (~20 eV) 401. It may be observed from the graph 400 that both the analyte profiles 402 and 403 of the patient show the presence of an abnormal peak 410 representing an unknown biomarker. The mass-to-charge ratio, intensity, and isotopic ratios of the peak 410 are then used to search in the reference library in order to identify the biomarker corresponding to the identified abnormal peak 410, and to determine the contamination level or the disease stage.

Then, at block 236, the process 200 asks if a new analysis is to be performed. If so, the process 200 proceeds to block 238, if not, the process 200 ends.

At block 238, the process 200 asks the user to clean the direct sample introduction interface 104. In an alternative embodiment, the direct sample introduction interface 104 may be provided with a cleaning mechanism using, for example, alcohol, water or heat, which may be activated by the process 200 and automatically clean up any contamination due to the last analysis performed. The needle may also be changed automatically. The process 200 then proceeds to block 240.

Finally, at block 240, the process 200 asks if the new analysis is for the same patient. If so, the process 200 proceeds to block 220 where the sample type is selected, if not, it proceeds to block 218 where the information about the new patient is entered.

Figure 3:
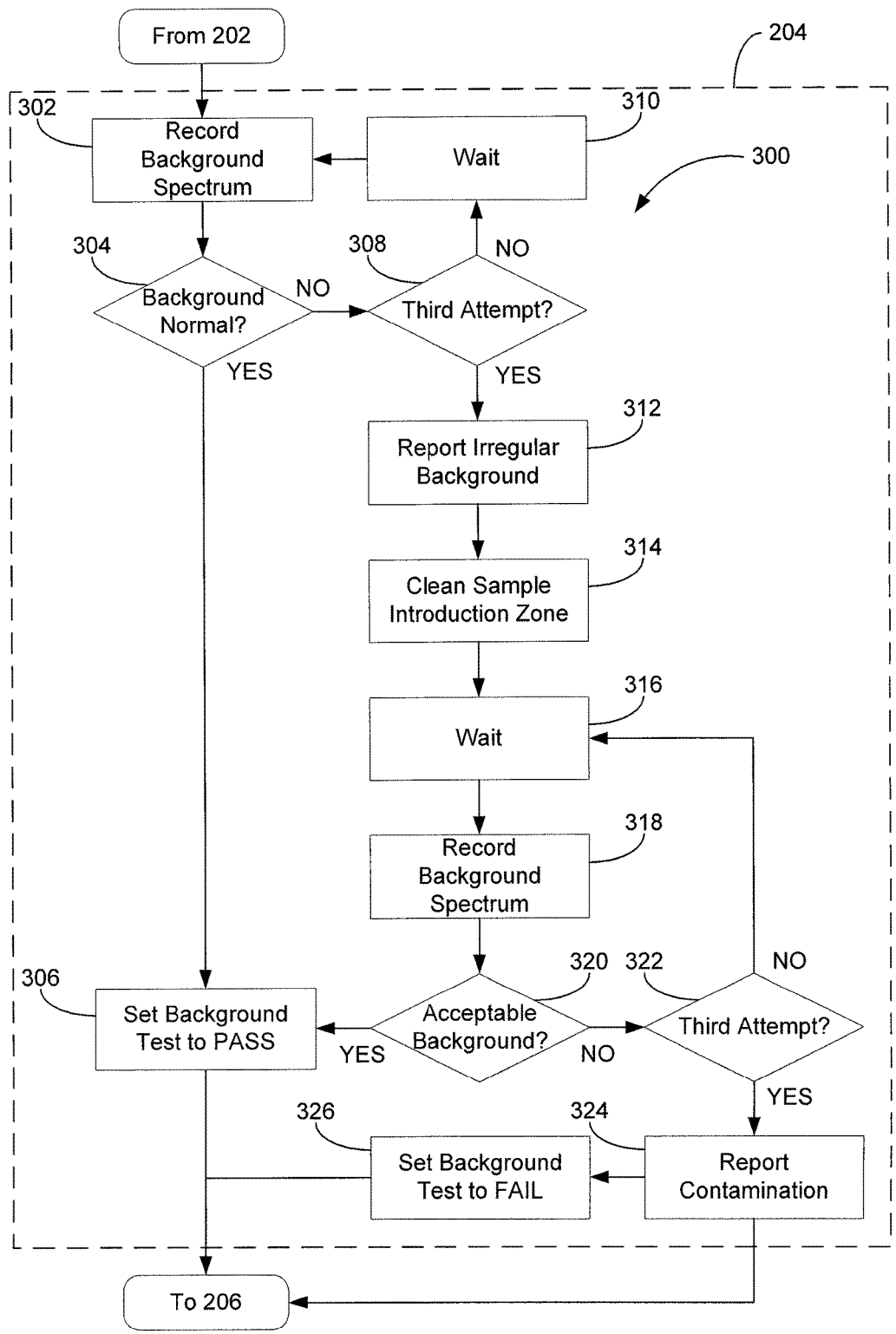
FIG. 3 is a flow diagram of an example of a background and surrounding environment analysis sub-process that may be used with the operating process of FIGS. 2A and 2B.

Referring now to FIG. 3, there is shown a flow diagram of an example of a background analysis sub-process 300 that may be executed by process 200 at block 204 of FIG. 2A. The steps of the sub-process 300 are indicated by blocks 302 to 326.

The sub-process 300 starts at block 302 where the background spectrum is recorded. Following which, at block 304, the sub-process 300 verifies if the background is normal by comparing the recorded background spectrum with that of reference background spectra stored in the database 120. If the background spectrum is normal, then the sub-process 300 proceeds to block 306 where the background test is set to "PASS". The sub-process 300 then hands over control back to process 200 of FIG. 2A, which then proceeds to block 206. If the background spectrum is not normal, then sub-process 300 proceeds to block 308.

At block 308, the sub-process 300 verifies if the background has been determined to be abnormal for the third time. If not, the sub-process 300 proceeds to block 310 where it pauses, for example by waiting for a few minutes (e.g. from 1 to 5 minutes) before proceeding back to block 302 for a new recording of the background spectrum. If the background has been determined to be abnormal for the third time, the sub-process 300 proceeds to block 312 where the presence of an irregular background is reported via the user interface 124. A listing of the detected compounds and contaminants, as well as their proportions, may also be communicated. These may be identified by comparing the abnormal peaks found in the background spectrum with spectra stored in the reference database 120.

At block 314, the sub-process 300 asks the user to clean the direct sample introduction interface 104. In an alternative embodiment, the direct sample introduction interface 104 may be provided with a cleaning mechanism using, for example, alcohol, water or heat, which may be activated by the sub-process 300 and automatically clean up any contamination due to the last analysis performed. The needle may also be changed automatically.

At block 316, sub-process 300 pauses for a few minutes (e.g. 1 to 3 minutes) before proceeding to block 318 where the background spectrum is recorded.

Then, at block 320, sub-process 300 verifies if the background spectrum is within an acceptable range of the reference background, for example 25%, and that no dangerous compounds or contaminants have been detected. If so, sub-process 300 proceeds to block 306, if not, it proceeds to block 322.

At block 322, the sub-process 300 verifies if the background has been determined not to be within an acceptable range of the reference background for the third time. If not, the sub-process 300 proceeds to block 316. If so, the sub-process 300 proceeds to block 324 where the presence of a contaminated environment is reported via the user interface 124. A listing of the detected compounds and contaminants, as well as their proportions, may also be communicated. Furthermore, should the detected compounds and contaminants, or their proportions, are found to be dangerous, the sub-process 300 instructs the user to evacuate the contaminated zone and, in an alternative embodiment, may sound an alarm and/or communicate the danger to a further system using the input/output interface 126. The sub-process 300 then proceeds to block 326 where the background analysis is set to "FAIL". The sub-process 300 then hands over control back to process 200 of FIG. 2A, which then proceeds to block 206.

It is to be understood that the number of repetitions of the background test at blocks 308 and 322, as well as the waiting times at blocks 310 and 316, as well as the range at block 320 may be adjusted.

It is also to be understood that the described diagnostic apparatus 100 can be used, provided that the appropriate spectra libraries are included in the database 120, as a real-time analyzer of biological or chemical contaminated areas, for:

indoor air quality: detection of chemical and biological contaminants in hospitals, schools, private and public buildings, plants, malls, planes, trains, etc.;
  environmental assessments: soil, water or air contamination;
  mining industry: exploration and analysis of soil mineral content;
  food industry: analysis of the food composition and detection of contaminants in the production chain;
  homeland security: monitoring of restricted areas in airports, ports, etc.; and
  other fields such as forensics, pharmaceuticasl, cosmetics, etc.

It is to be understood that although reference has been made to the peak and mass patterns being used for the identification of biomarkers, they may also be used to identify an indicator which may be a biomarker, a chemical compound, a chemical element, a mineral, etc., depending on the application. Furthermore, depending on the application, the diagnosis may be a report listing contaminants, mineral composition, oil presence, etc.

Although the present invention has been described by way of a particular embodiment and examples thereof, it should be noted that it will be apparent to persons skilled in the art that modifications may be applied to the present particular embodiment without departing from the scope of the present invention.

What is claimed:

1. A portable plasma based real time medical diagnostic apparatus, comprising:
   an atmospheric plasma source for producing energetic projectiles;
   a high pressure environment mass analyzer operating at a pressure between $10^{-4}$ and $10^{-1}$ mbar;
   an atmospheric direct sample introduction interface having a space for directly receiving from a patient-an untreated patient specimen to be analyzed, the atmospheric direct sample introduction interface being at atmospheric pressure and positioned between the plasma source and the mass analyzer;
   a database containing a reference library of chemical and/or biological reference materials, each reference material having an associated mass spectrum, health condition and probability of the health condition being present, and chemical and/or biological fingerprints of healthy patients;
   a processor operatively connected to the plasma source, the mass analyzer and the database, the processor being so programmed so as to:
   obtain from the mass analyzer a patient specimen mass spectrum of parent and fragment ions resulting from collisions between the energetic projectiles and the untreated patient specimen present in the space of the atmospheric direct sample introduction interface;
   generate a chemical and/or biological fingerprint of the patient using the peaks in the patient specimen mass spectrum;
   identify abnormal mass spectrum peaks in the chemical and/or biological fingerprint of the patient by comparing the chemical and/or biological fingerprint of the patient with the chemical and/or biological fingerprints of healthy patients in the database;
   compare the identified abnormal mass spectrum peaks with the mass spectra of the chemical and/or biological reference materials in the reference library in order to identify at least one corresponding chemical and/or biological reference material; and
   provide a diagnosis of the patient based on the health condition and the probability of the health condition being present associated with the identified at least one corresponding chemical and/or biological reference material.

2. An apparatus according to claim 1, wherein the processor is further so configured so as to subtract a background spectrum from the patient specimen mass spectrum.

3. An apparatus according to claim 1, wherein the patient specimen is biological tissue.

4. An apparatus according to claim 1, wherein the atmospheric direct sample introduction interface includes a needle mechanism for taking a blood drop sample from the patient.

5. An apparatus according to claim 1, wherein the health condition is selected from the group consisting of infections, metabolic disorders, cancers and malignancy diseases.

6. An apparatus according to claim 1, wherein the analyzer chamber further includes a high pressure ions detector operatively connected to a plurality of ion extraction and transport lens, the high pressure ions detector and the plurality of ion extraction and transport lens cooperating so as to extract parent and fragment ions and focus the extracted parent and fragment ions at an entrance of the mass analyzer.

7. An apparatus according to claim 1, wherein the energetic projectiles are selected from a group consisting of plasma, atoms, photons, electrons and ions.

8. An apparatus according to claim 1, wherein the plasma source has a volume equal or less than 0.175 cm$^3$.

9. An apparatus according to claim 8, wherein the plasma source has a gas density between $10^{13}$ and $10^{15}$ particles/mm$^3$.

10. An apparatus according to claim 8, wherein the plasma source has a downstream flow between $10^{16}$ and $10^{19}$ particles/sec.

11. An apparatus according to claim 1, wherein the patient specimen is selected from the group consisting of skin, blood, saliva and urine.

12. An apparatus according to claim 1, wherein the patient specimen is in a state selected from the group consisting of solid, liquid and gaseous.

\* \* \* \* \*